(12) United States Patent
Belghoul et al.

(10) Patent No.: US 10,433,211 B2
(45) Date of Patent: Oct. 1, 2019

(54) DYNAMIC LINK MONITORING TO RESOLVE IMBALANCE IN LAA/LTE RADIO RESOURCE ALLOCATION

(71) Applicant: Apple Inc., Cupertino, CA (US)

(72) Inventors: Farouk Belghoul, Campbell, CA (US); Lydi Smaini, San Jose, CA (US); Tarik Tabet, Los Gatos, CA (US); Syed Aon Mujtaba, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 97 days.

(21) Appl. No.: 15/593,702

(22) Filed: May 12, 2017

(65) Prior Publication Data

US 2018/0020376 A1    Jan. 18, 2018

Related U.S. Application Data

(60) Provisional application No. 62/361,995, filed on Jul. 13, 2016.

(51) Int. Cl.
*H04W 28/08* (2009.01)
*H04W 16/14* (2009.01)
*H04W 72/04* (2009.01)

(52) U.S. Cl.
CPC ......... *H04W 28/085* (2013.01); *H04W 16/14* (2013.01); *H04W 72/0453* (2013.01)

(58) Field of Classification Search
CPC .................................................. H04W 28/085
See application file for complete search history.

(56) References Cited

U.S. PATENT DOCUMENTS

| 8,965,390 B2 | 2/2015 | Morrison |
| 9,560,651 B2 | 1/2017 | Wilhelmsson et al. |
| 2014/0362780 A1* | 12/2014 | Malladi ................. H04W 16/14 370/329 |
| 2015/0063151 A1* | 3/2015 | Sadek ................... H04W 24/08 370/252 |

(Continued)

OTHER PUBLICATIONS

Office Action, Korean Patent Application No. 10-2017-0086507, dated Aug. 23, 2018, six pages.

*Primary Examiner* — Jason E Mattis
(74) *Attorney, Agent, or Firm* — Meyertons Hood Kivlin Kowert and Goetzel PC; Jeffrey C. Hood

(57) ABSTRACT

A wireless communication device (UE) may monitor grants received from respective cells associated with one or more first (e.g. licensed) frequency band(s) and one or more second (e.g. unlicensed) frequency band(s). Based on the received grants the UE may determine if an imbalance exists in the radio resource allocation, whereby the UE communicates more than intended in the second frequency band(s). The imbalance may be specified with respect to the ratio or portion of the communications that are conducted in the second frequency band(s) with respect to all wireless communications of the UE. If the UE detects an imbalance, it may transmit a report to the network (e.g. to the base station serving the UE) indicating unfavorable conditions for the UE to be operating in the second frequency band(s). In response, the network may disable the respective cell(s) associated with the second frequency band(s) and/or it may disable carrier aggregation for the UE.

21 Claims, 7 Drawing Sheets

(56) References Cited

U.S. PATENT DOCUMENTS

| | | |
|---|---|---|
| 2015/0172032 A1* | 6/2015 | Khay-Ibbat ............ H04L 5/0057 370/329 |
| 2015/0295832 A1* | 10/2015 | Cotter ................... H04L 47/125 370/235 |
| 2016/0014798 A1 | 1/2016 | Cheng et al. |
| 2016/0095110 A1 | 3/2016 | Li |
| 2016/0156548 A1* | 6/2016 | Pazhyannur .......... H04W 28/08 370/338 |
| 2016/0157230 A1 | 6/2016 | Nord |
| 2016/0157293 A1 | 6/2016 | Pazhyannur |
| 2016/0183243 A1 | 6/2016 | Park et al. |
| 2017/0127327 A1* | 5/2017 | Newbury ............ H04W 28/085 |
| 2018/0352590 A1* | 12/2018 | Sha ....................... H04W 76/27 |

* cited by examiner

DYNAMIC LINK MONITORING TO RESOLVE IMBALANCE IN LAA/LTE RADIO RESOURCE ALLOCATION

PRIORITY CLAIM

This application claims benefit of priority of U.S. Provisional Patent Application Ser. No. 62/361,995 titled "Dynamic Link Monitoring to Resolve Imbalance in LAA/LTE Radio Resource Allocation", filed on Jul. 13, 2016, which is hereby incorporated by reference as though fully and completely set forth herein.

FIELD OF THE INVENTION

The present application relates to wireless communications, and more particularly to radio resource allocation during LAA/LTE communications.

DESCRIPTION OF THE RELATED ART

Wireless communication systems are rapidly growing in usage. In recent years, wireless devices such as smart phones and tablet computers have become increasingly sophisticated. In addition to supporting telephone calls, many mobile devices (i.e., user equipment devices or UEs) now provide access to the internet, email, text messaging, and navigation using the global positioning system (GPS), and are capable of operating sophisticated applications that utilize these functionalities. Additionally, there exist numerous different wireless communication technologies and standards. Some examples of wireless communication standards include GSM, UMTS (WCDMA, TDS-CDMA), LTE, LTE Advanced (LTE-A), HSPA, 3GPP2 CDMA2000 (e.g., 1xRTT, 1xEV-DO, HRPD, eHRPD), IEEE 802.11 (WLAN or Wi-Fi), IEEE 802.16 (WiMAX), BLUETOOTH™, etc.

The ever increasing number of features and functionality introduced in wireless communication devices also creates a continuous need for improvement in both wireless communications and in wireless communication devices. In particular, it is important to ensure the accuracy of transmitted and received signals through user equipment (UE) devices, e.g., through wireless devices such as cellular phones, base stations and relay stations used in wireless cellular communications. In addition, increasing the functionality of a UE device can place a significant strain on the battery life of the UE device. Thus it is very important to also reduce power requirements in UE device designs while allowing the UE device to maintain good transmit and receive abilities for improved communications.

The UEs, which may be mobile telephones or smart phones, portable gaming devices, laptops, wearable devices, PDAs, tablets, portable Internet devices, music players, data storage devices, or other handheld devices, etc. may have multiple radio interfaces that enable support of multiple radio access technologies (RATs) as defined by the various wireless communication standards (LTE, LTE-A, Wi-Fi, BLUETOOTH™, etc.). The radio interfaces may be used by various applications and the presence of the multiple radio interfaces may necessitate the UE to implement mobility solutions to seamlessly run applications simultaneously over multiple radio interfaces (e.g., over LTE/LTE-A and BLUETOOTH™) without impacting the end-to-end performance of the application. That is, the UE may need to implement mobility solutions to simultaneously operate multiple radio interfaces corresponding to multiple RATs (e.g., LTE/LTE-A, Wi-Fi, BLUETOOTH™, etc.).

In addition to the communication standards mentioned above, there also exist extensions aimed at boosting transmission coverage in certain cellular networks. For example, LTE in Unlicensed spectrum (LTE-U) allows cellphone carriers to boost coverage in their cellular networks by transmitting in the unlicensed 5 GHz band which is also used by many Wi-Fi devices. License Assisted Access (LAA) describes a similar technology aimed to standardize operation of LTE in the Wi-Fi bands through the use of a contention protocol referred to as listen-before-talk (LBT), which facilitates coexistence with other Wi-Fi devices on the same band. In some cases the coexistence of cellular and Wi-Fi communications in the same band can result in the degradation of data throughput and/or decreased performance of streaming applications (data streaming) when both Wi-Fi signals and LAA/LTE-U signals are present. Furthermore, cellular communications conducted in the unlicensed band(s) oftentimes require increased power consumption in comparison to cellular communications conducted in the licensed band(s).

Other corresponding issues related to the prior art will become apparent to one skilled in the art after comparing such prior art with the disclosed embodiments as described herein.

SUMMARY OF THE INVENTION

Embodiments are presented herein of, inter alia, of methods for detecting an imbalance between cellular communications conducted in a first specified spectrum, e.g. in a licensed band, and cellular communications conducted in a second specified spectrum, e.g. in an unlicensed band, by a wireless communication device, and mitigating the impact of the imbalance on the performance and/or power consumption of the wireless communication device. The imbalance in radio resource allocation patterns and thresholds may be defined according to device, type of applications, type of radio bearers and/or IP flows. Embodiments are further presented herein for wireless communication systems containing user equipment (UE) devices and/or base stations communicating with each other within the wireless communication systems.

In some embodiments, a wireless communication device may conduct wireless communications over (or in) a first specified frequency band (or spectrum) according to a first radio access technology (RAT), where the first RAT may represent cellular wireless communications. The wireless communication device may also simultaneously conduct wireless communications over (or) in a second specified frequency band (or spectrum) according to the first RAT. The first frequency band may be a licensed band associated with the first RAT, e.g. a licensed band associated with 3GPP communications, and the second frequency band may be an unlicensed band associated with the first RAT, such as a frequency band also associated with a second RAT, e.g. a 5 GHz band also associated with Wi-Fi communications. The wireless communication device may detect an imbalance between the communications conducted according to the first RAT over the first frequency band (or spectrum) and the second frequency band (or spectrum), and upon detecting this imbalance, take corrective action(s) to adjust the respective portions of the wireless communications conducted according to the first RAT by the wireless communication device over the first specified frequency band and the second specified frequency band. Specifically, the wireless communication device may detect when more of the wireless communications are conducted over the second specified frequency band (e.g. over the unlicensed band) that a previously determined or specified portion of the overall wireless communications conducted by the wireless communication device according to the first RAT, and make adjustments to have the wireless communication device conduct more of the wireless communications according to the first RAT over the first specified frequency band (e.g. over the licensed band) than over the second specified frequency band.

Accordingly, a wireless communication device may conduct wireless communications according to a first radio access technology (RAT) simultaneously in a first frequency band and in a second frequency band, and may detect a radio resource allocation imbalance manifested at least in the wireless communication device conducting a higher portion of the wireless communications in the second frequency band with respect to the first frequency band than a previously specified portion, and in response to detecting the radio resource allocation imbalance, cause a base station serving the wireless communication device to schedule subsequent wireless communications of the wireless communication device to take place in the first frequency band. The first frequency band may represent a licensed frequency band for the wireless communications while the second frequency band may represent an unlicensed frequency band for the wireless communications. The wireless communication device may detect the radio resource allocation imbalance by executing an algorithm integrated into a media access control layer, tracking grants received by the wireless communication device and respectively associated with a primary cell associated with the first frequency band and secondary cell(s) associated with the second frequency band. For example, the wireless communication device may detect that the wireless communication device successively received at least a specified number of grants associated with the secondary cell(s), for a specific transmit time interval, and interpret this as an imbalance in the radio resource allocation. In another example, the wireless communication device may receive a first number of grants associated with the primary cell and a second number of grants associated with the secondary cell(s), and if the second number exceeds the first number by at least a specified amount, then the wireless communication device may interpret that as an imbalance in the radio resource allocation. The specified amount may be set to be different for each different type of traffic included in the wireless communications, such as VoLTE, Best Effort, etc. Specifically, different specified amounts may be determined based on the quality of service (QoS) associated with various types of traffic. For example, the specified amount (or threshold) may be different for a first QoS associated with certain types of traffic than for a second QoS associated with other types of traffic. In yet some other embodiments, the wireless communication device may track how many grants associated with the primary cell associated and how many grants associated with the secondary cell(s) are received by the wireless communication device for a transmit time interval to determine if there is a radio resource allocation imbalance.

In some embodiments, the base station may schedule the subsequent wireless communications of the wireless communication device in the first frequency band by deactivating the secondary cell(s) and/or deactivating carrier aggregation for the wireless communication device. In some embodiments, the wireless communication device may transmit a channel quality indicator value of zero for the secondary cell(s) to the base station to cause the deactivation of the secondary cell(s) by the base station. In general, the wireless communication device may transmit a report to the base station, with the report indicative of unfavorable conditions for the wireless communication device to be operating in the second frequency band, in response to which the base station may schedule subsequent wireless communications of the wireless communication device to take place in the first frequency band.

Note that the techniques described herein may be implemented in and/or used with a number of different types of devices, including but not limited to, base stations, access points, cellular phones, portable media players, tablet computers, wearable devices, and various other computing devices.

This Summary is intended to provide a brief overview of some of the subject matter described in this document. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

Figure 1:
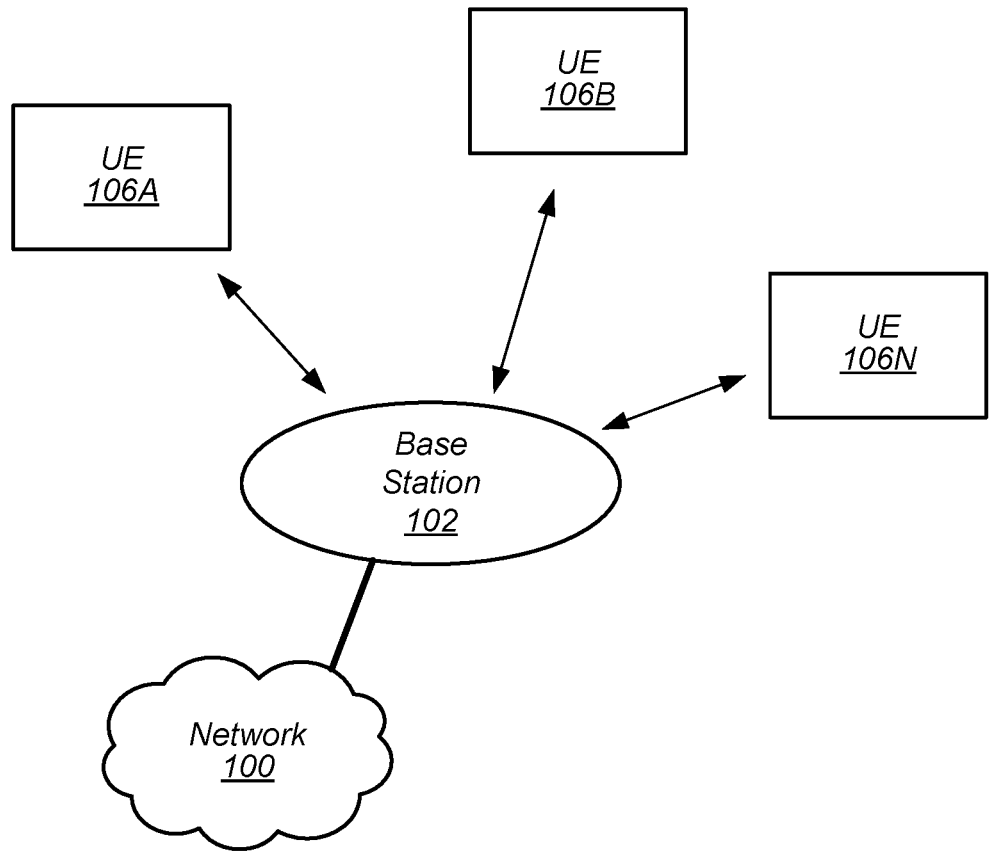
FIG. 1 illustrates an exemplary (and simplified) wireless communication system, according to some embodiments.

While features described herein are susceptible to various modifications and alternative forms, specific embodiments thereof are shown by way of example in the drawings and are herein described in detail. It should be understood, however, that the drawings and detailed description thereto are not intended to be limiting to the particular form disclosed, but on the contrary, the intention is to cover all modifications, equivalents and alternatives falling within the spirit and scope of the subject matter as defined by the appended claims.

DETAILED DESCRIPTION OF THE EMBODIMENTS

Acronyms

Various acronyms are used throughout the present application. Definitions of the most prominently used acronyms that may appear throughout the present application are provided below:

ACK: Acknowledgement
APR: Applications Processor

BS: Base Station
BSR: Buffer Size Report
CC: Component Carrier
CMR: Change Mode Request
CQI: Channel Quality Indicator
DL: Downlink (from BS to UE)
DYN: Dynamic
FDD: Frequency Division Duplexing
FT: Frame Type
GPRS: General Packet Radio Service
GSM: Global System for Mobile Communication
HARQ: Hybrid Automatic Repeat Request
IE: Information Element
LAN: Local Area Network
LBT: Listen Before Talk
LTE: Long Term Evolution
LTE-U: LTE in Unlicensed Spectrum
LAA: License Assisted Access
MAC: Media Access Control (layer)
NACK: Negative Acknowledgement
PCell: Primary Cell
PDCCH: Physical Downlink Control Channel
PDSCH: Physical Downlink Shared Channel
PDN: Packet Data Network
PDU: Protocol Data Unit
PUCCH: Physical Uplink Control Channel
QoS: Quality of Service
RAT: Radio Access Technology
RF: Radio Frequency
RTP: Real-time Transport Protocol
RX: Reception/Receive
SCell: Secondary Cell
TBS: Transport Block Size
TDD: Time Division Duplexing
TTI: Transmission Time Interval
TX: Transmission/Transmit
UCI: Uplink Control Information
UE: User Equipment (Device)
UL: Uplink (from UE to BS)
UMTS: Universal Mobile Telecommunication System
VoLTE: Voice over LTE
WLAN: Wireless LAN
Wi-Fi: Wireless Local Area Network (WLAN) RAT based on the Institute of Electrical and Electronics Engineers' (IEEE) 802.11 standards Terms The Following is a Glossary of Terms that may Appear in the Present Application:

Memory Medium—Any of various types of memory devices or storage devices. The term "memory medium" is intended to include an installation medium, e.g., a CD-ROM, floppy disks, or tape device; a computer system memory or random access memory such as DRAM, DDR RAM, SRAM, EDO RAM, Rambus RAM, etc.; a non-volatile memory such as a Flash, magnetic media, e.g., a hard drive, or optical storage; registers, or other similar types of memory elements, etc. The memory medium may comprise other types of memory as well or combinations thereof. In addition, the memory medium may be located in a first computer system in which the programs are executed, or may be located in a second different computer system which connects to the first computer system over a network, such as the Internet. In the latter instance, the second computer system may provide program instructions to the first computer system for execution. The term "memory medium" may include two or more memory mediums which may reside in different locations, e.g., in different computer systems that are connected over a network.

Carrier Medium—a memory medium as described above, as well as a physical transmission medium, such as a bus, network, and/or other physical transmission medium that conveys signals such as electrical, electromagnetic, or digital signals.

Computer System (or Computer)—any of various types of computing or processing systems, including a personal computer system (PC), mainframe computer system, workstation, network appliance, Internet appliance, personal digital assistant (PDA), television system, grid computing system, or other device or combinations of devices. In general, the term "computer system" may be broadly defined to encompass any device (or combination of devices) having at least one processor that executes instructions from a memory medium.

User Equipment (UE) (or "UE Device")—any of various types of computer systems devices which are mobile or portable and which performs wireless communications. Also referred to as wireless communication devices. Examples of UE devices include mobile telephones or smart phones (e.g., iPhone™, Android™-based phones) and tablet computers such as iPad™, Samsung Galaxy™, etc., portable gaming devices (e.g., Nintendo DS™, Play Station Portable™, Gameboy Advance™, iPod™), laptops, wearable devices (e.g. Apple Watch™, Google Glass™) PDAs, portable Internet devices, music players, data storage devices, or other handheld devices, etc. Various other types of devices would fall into this category if they include Wi-Fi or both cellular and Wi-Fi communication capabilities and/or other wireless communication capabilities, for example over short-range radio access technologies (SRATs) such as BLUETOOTH™, etc. In general, the term "UE" or "UE device" may be broadly defined to encompass any electronic, computing, and/or telecommunications device (or combination of devices) which is easily transported by a user and capable of wireless communication.

Base Station (BS)—The term "Base Station" has the full breadth of its ordinary meaning, and at least includes a wireless communication station installed at a fixed location and used to communicate as part of a wireless telephone system or radio system.

Processing Element—refers to various elements or combinations of elements that are capable of performing a function in a device, e.g. in a user equipment device or in a cellular network device. Processing elements may include, for example: processors and associated memory, portions or circuits of individual processor cores, entire processor cores, processor arrays, circuits such as an ASIC (Application Specific Integrated Circuit), programmable hardware elements such as a field programmable gate array (FPGA), as well any of various combinations of the above.

Wireless Device (or wireless communication device)—any of various types of computer systems devices which performs wireless communications using WLAN communications, SRAT communications, Wi-Fi communications and the like. As used herein, the term "wireless device" may refer to a UE device, as defined above, or to a stationary device, such as a stationary wireless client or a wireless base station. For example a wireless device may be any type of wireless station of an 802.11 system, such as an access point (AP) or a client station (UE), or any type of wireless station of a cellular communication system communicating according to a cellular radio access technology (e.g. LTE, CDMA, GSM), such as a base station or a cellular telephone, for example.

Wi-Fi—The term "Wi-Fi" has the full breadth of its ordinary meaning, and at least includes a wireless communication network or RAT that is serviced by wireless LAN (WLAN) access points and which provides connectivity through these access points to the Internet. Most modern Wi-Fi networks (or WLAN networks) are based on IEEE 802.11 standards and are marketed under the name "Wi-Fi". A Wi-Fi (WLAN) network is different from a cellular network.

Automatically—refers to an action or operation performed by a computer system (e.g., software executed by the computer system) or device (e.g., circuitry, programmable hardware elements, ASICs, etc.), without user input directly specifying or performing the action or operation. Thus the term "automatically" is in contrast to an operation being manually performed or specified by the user, where the user provides input to directly perform the operation. An automatic procedure may be initiated by input provided by the user, but the subsequent actions that are performed "automatically" are not specified by the user, i.e., are not performed "manually", where the user specifies each action to perform. For example, a user filling out an electronic form by selecting each field and providing input specifying information (e.g., by typing information, selecting check boxes, radio selections, etc.) is filling out the form manually, even though the computer system must update the form in response to the user actions. The form may be automatically filled out by the computer system where the computer system (e.g., software executing on the computer system) analyzes the fields of the form and fills in the form without any user input specifying the answers to the fields. As indicated above, the user may invoke the automatic filling of the form, but is not involved in the actual filling of the form (e.g., the user is not manually specifying answers to fields but rather they are being automatically completed). The present specification provides various examples of operations being automatically performed in response to actions the user has taken.

Configured to—Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph six, interpretation for that component.

Figure 2:
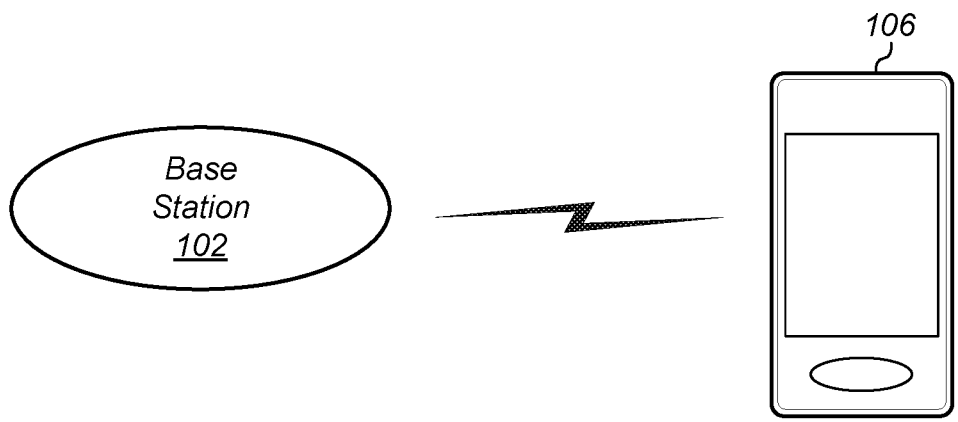
FIG. 2 illustrates an exemplary base station in communication with an exemplary wireless user equipment (UE) device, according to some embodiments.

FIGS. 1 and 2—Exemplary Communication System

FIG. 1 illustrates an exemplary (and simplified) wireless communication system, according to some embodiments. It is noted that the system of FIG. 1 is merely one example of a possible system, and embodiments may be implemented in any of various systems, as desired.

As shown, the exemplary wireless communication system includes a base station 102 which communicates over a transmission medium with one or more user devices 106-1 through 106-N. Each of the user devices may be referred to herein as a "user equipment" (UE) or UE device. Thus, the user devices 106 are referred to as UEs or UE devices. Various ones of the UE devices may perform dynamic link monitoring and resolve imbalance in LAA/LTE radio resource allocation as detailed herein.

The base station 102 may be a base transceiver station (BTS) or cell site, and may include hardware that enables wireless communication with the UEs 106A through 106N. The base station 102 may also be equipped to communicate with a network 100 (e.g., a core network of a cellular service provider, a telecommunication network such as a public switched telephone network (PSTN), and/or the Internet, among various possibilities). Thus, the base station 102 may facilitate communication between the user devices and/or between the user devices and the network 100. The communication area (or coverage area) of the base station may be referred to as a "cell." It should also be noted that "cell" may also refer to a logical identity for a given coverage area at a given frequency. In general, any independent cellular wireless coverage area may be referred to as a "cell". In such cases a base station may be situated at particular confluences of three cells. The base station, in this uniform topology, may serve three 120 degree beam width areas referenced as cells. Also, in case of carrier aggregation, small cells, relays, etc. may each represent a cell. Thus, in carrier aggregation in particular, there may be primary cells and secondary cells which may service at least partially overlapping coverage areas but on different respective frequencies. For example, a base station may serve any number of cells, and cells served by a base station may or may not be collocated (e.g. remote radio heads). As also used herein, from the perspective of UEs, a base station may sometimes be considered as representing the network insofar as uplink and downlink communications of the UE are concerned. Thus, a UE communicating with one or more base stations in the network may also be interpreted as the UE communicating with the network.

The base station 102 and the user devices may be configured to communicate over the transmission medium using any of various radio access technologies (RATs), also referred to as wireless communication technologies, or telecommunication standards, such as GSM, UMTS (WCDMA), LTE, LTE-Advanced (LTE-A), LAA/LTE-U, 3GPP2 CDMA2000 (e.g., 1xRTT, 1xEV-DO, HRPD, eHRPD), Wi-Fi, WiMAX etc. In some embodiments, the base station 102 communicates with at least one UE using improved UL (Uplink) and DL (Downlink) decoupling, preferably through LTE or a similar RAT standard.

UE 106 may be capable of communicating using multiple wireless communication standards. For example, a UE 106 might be configured to communicate using either or both of a 3GPP cellular communication standard (such as LTE) or a 3GPP2 cellular communication standard (such as a cellular communication standard in the CDMA2000 family of cellular communication standards). In some embodiments, the UE 106 may be configured to perform dynamic link monitoring and resolve imbalance in LAA/LTE radio resource allocation, at least according to the various methods as described herein. Base station 102 and other similar base stations operating according to the same or a different cellular communication standard may thus be provided as one or more networks of cells, which may provide continuous or nearly continuous overlapping service to UE 106 and similar devices over a wide geographic area via one or more cellular communication standards.

The UE 106 might also or alternatively be configured to communicate using WLAN, BLUETOOTH™, one or more global navigational satellite systems (GNSS, e.g., GPS or GLONASS), one and/or more mobile television broadcasting standards (e.g., ATSC-M/H or DVB-H), etc. Other combinations of wireless communication standards (including more than two wireless communication standards) are also possible.

FIG. 2 illustrates an exemplary user equipment 106 (e.g., one of the devices 106-1 through 106-N) in communication with the base station 102, according to some embodiments. The UE 106 may be a device with wireless network connectivity such as a mobile phone, a hand-held device, a computer or a tablet, or virtually any type of wireless device. The UE 106 may include a processor that is configured to execute program instructions stored in memory. The UE 106 may perform any of the method embodiments described herein by executing such stored instructions. Alternatively, or in addition, the UE 106 may include a programmable hardware element such as an FPGA (field-programmable gate array) that is configured to perform any of the method embodiments described herein, or any portion of any of the method embodiments described herein. The UE 106 may be configured to communicate using any of multiple wireless communication protocols. For example, the UE 106 may be configured to communicate using two or more of CDMA2000, LTE, LTE-A, WLAN, or GNSS. Other combinations of wireless communication standards are also possible.

The UE 106 may include one or more antennas for communicating using one or more wireless communication protocols according to one or more RAT standards. In some embodiments, the UE 106 may share one or more parts of a receive chain and/or transmit chain between multiple wireless communication standards. The shared radio may include a single antenna, or may include multiple antennas (e.g., for MIMO) for performing wireless communications. Alternatively, the UE 106 may include separate transmit and/or receive chains (e.g., including separate antennas and other radio components) for each wireless communication protocol with which it is configured to communicate. As another alternative, the UE 106 may include one or more radios which are shared between multiple wireless communication protocols, and one or more radios which are used exclusively by a single wireless communication protocol. For example, the UE 106 may include a shared radio for communicating using either of LTE or CDMA2000 1xRTT, and separate radios for communicating using each of Wi-Fi and BLUETOOTH™. Other configurations are also possible.

Figure 3:
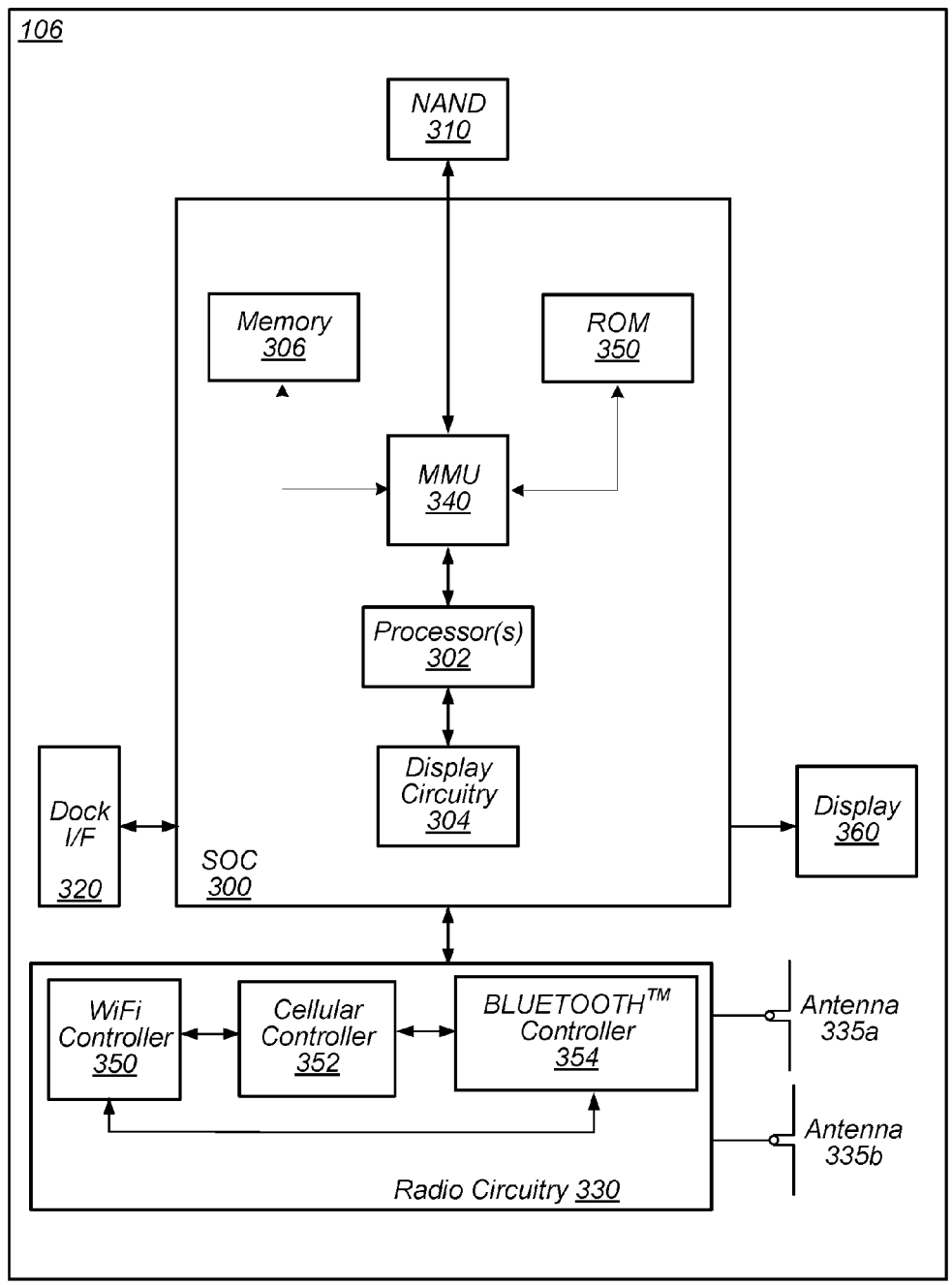
FIG. 3 illustrates an exemplary block diagram of a UE, according to some embodiments.

FIG. 3—Block Diagram of an Exemplary UE

FIG. 3 illustrates a block diagram of an exemplary UE 106, according to some embodiments. As shown, the UE 106 may include a system on chip (SOC) 300, which may include portions for various purposes. For example, as shown, the SOC 300 may include processor(s) 302 which may execute program instructions for the UE 106 and display circuitry 304 which may perform graphics processing and provide display signals to the display 360. The processor(s) 302 may also be coupled to memory management unit (MMU) 340, which may be configured to receive addresses from the processor(s) 302 and translate those addresses to locations in memory (e.g., memory 306, read only memory (ROM) 350, NAND flash memory 310) and/or to other circuits or devices, such as the display circuitry 304, radio circuitry 330, connector I/F 320, and/or display 360. The MMU 340 may be configured to perform memory protection and page table translation or set up. In some embodiments, the MMU 340 may be included as a portion of the processor(s) 302.

As shown, the SOC 300 may be coupled to various other circuits of the UE 106. For example, the UE 106 may include various types of memory (e.g., including NAND flash 310), a connector interface 320 (e.g., for coupling to the computer system), the display 360, and wireless communication circuitry (e.g., for LTE, LTE-A, CDMA2000, BLUETOOTH™, Wi-Fi, GPS, etc.). The UE device 106 may include at least one antenna (e.g. 335*a*), and possibly multiple antennas (e.g. illustrated by antennas 335*a* and 335*b*), for performing wireless communication with base stations and/or other devices. Antennas 335*a* and 335*b* are shown by way of example, and UE device 106 may include fewer or more antennas. Overall, the one or more antennas are collectively referred to as antenna(s) 335. For example, the UE device 106 may use antenna(s) 335 to perform the wireless communication with the aid of radio circuitry 330. As noted above, the UE may be configured to communicate wirelessly using multiple wireless communication standards in some embodiments.

As described further subsequently herein, the UE 106 (and/or base station 102) may include hardware and software components for implementing methods for at least UE 106 to detect an imbalance between the respective communications of UE 106 over a first specified frequency band, which may be representative of a licensed spectrum (licensed frequency band), and over a second specified frequency band, which may be representative of an unlicensed spectrum (unlicensed frequency band). UE 106 may adjust its operations to address this imbalance, should such an imbalance be detected by UE 106. Thus, in some embodiments, UE 106 may detect when UE 106 is conducting a certain amount or a certain portion or a certain percentage of its cellular wireless communications (for example more than a specified percentage of all cellular communications of UE 106) over a first specified frequency band (e.g. over an unlicensed spectrum) versus conducting its cellular wireless communications over a second specified frequency band (e.g. a licensed spectrum), and may make operational adjustments accordingly. The processor(s) 302 of the UE device 106 may be configured to implement part or all of the methods described herein, e.g., by executing program instructions stored on a memory medium (e.g., a non-transitory computer-readable memory medium). In other embodiments, processor(s) 302 may be configured as a programmable hardware element, such as an FPGA (Field Programmable Gate Array), or as an ASIC (Application Specific Integrated Circuit). Furthermore, processor(s) 302 may be coupled to and/or may interoperate with other components as shown in FIG. 3, to implement communications by UE 106 that incorporate mitigating the potential effects of LAA/LTE imbalance for wireless communications of UE 106, according to various embodiments disclosed herein. Specifically, processor(s) 302 may be coupled to and/or may interoperate with other components as shown in FIG. 3 to facilitate UE 106 communicating in a manner that seeks to minimize imbalance between LAA and LTE communications of UE 106. Processor(s) 302 may also implement various other applications and/or end-user applications running on UE 106. It should also be noted that processor(s) 302 may be representative of multiple processing elements, interoperable to perform any or all of various applications and end-user applications and/or to perform part or all of the methods described herein.

In some embodiments, radio 300 may include separate controllers dedicated to controlling communications for various respective RAT standards. For example, as shown in FIG. 3, radio circuitry 330 may include a Wi-Fi controller 350, a cellular controller (e.g. LTE/3GPP controller) 352, and BLUETOOTH™ controller 354, and in at least some embodiments, one or more or all of these controllers may be implemented as respective integrated circuits (ICs or chips, for short) in communication with each other and with SOC 300 (and more specifically with processor(s) 302). For example, Wi-Fi controller 350 may communicate with cellular controller 352 over a cell-ISM link or WCI interface, and/or BLUETOOTH™ controller 354 may communicate with cellular controller 352 over a cell-ISM link, etc. While three separate controllers are illustrated within radio circuitry 330, other embodiments have fewer or more similar controllers for various different RATs that may be implemented in UE device 106.

Figure 4:
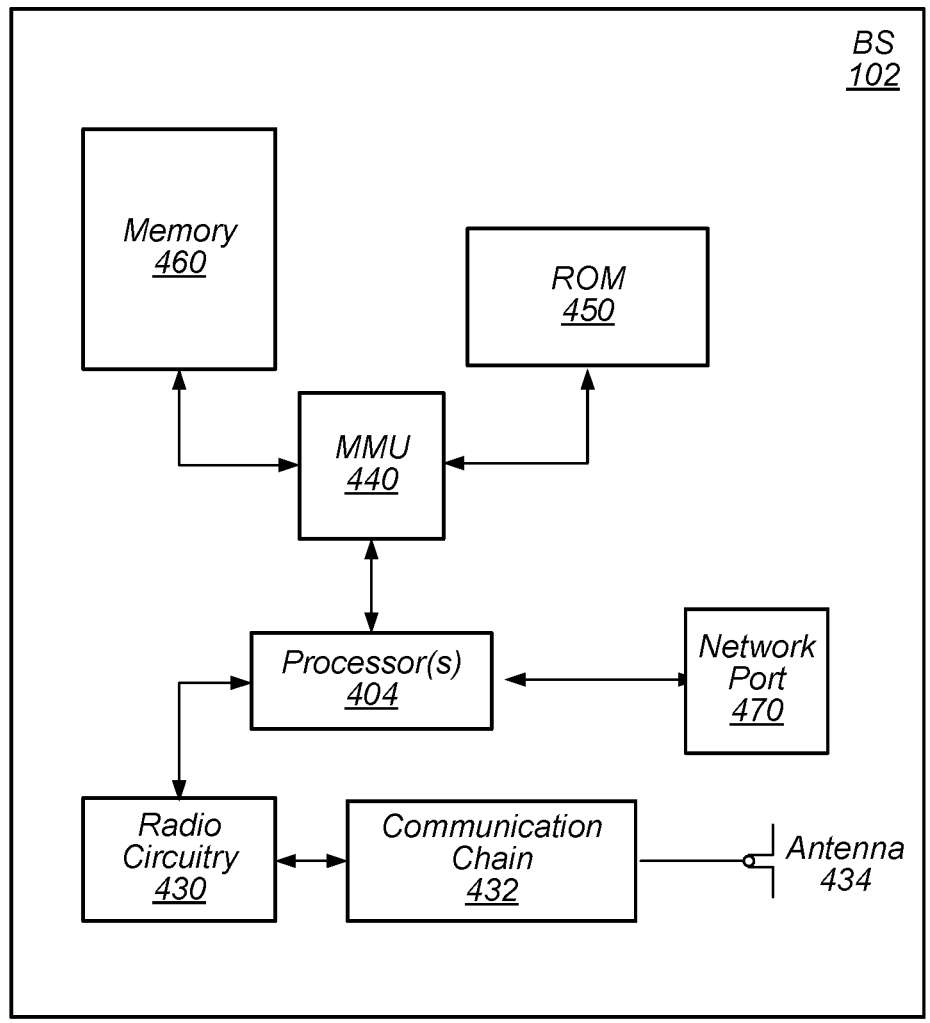
FIG. 4 illustrates an exemplary block diagram of a base station, according to some embodiments.

FIG. 4—Block Diagram of an Exemplary Base Station

FIG. 4 illustrates a block diagram of an exemplary base station 102, according to some embodiments. It is noted that the base station of FIG. 4 is merely one example of a possible base station. As shown, the base station 102 may include processor(s) 404 which may execute program instructions for the base station 102. The processor(s) 404 may also be coupled to memory management unit (MMU) 440, which may be configured to receive addresses from the processor(s) 404 and translate those addresses to locations in memory (e.g., memory 460 and read only memory (ROM) 450) or to other circuits or devices.

The base station 102 may include at least one network port 470. The network port 470 may be configured to couple to a telephone network and provide a plurality of devices, such as UE devices 106, access to the telephone network as described above in FIGS. 1 and 2. The network port 470 (or an additional network port) may also or alternatively be configured to couple to a cellular network, e.g., a core network of a cellular service provider. The core network may provide mobility related services and/or other services to a plurality of devices, such as UE devices 106. In some cases, the network port 470 may couple to a telephone network via the core network, and/or the core network may provide a telephone network (e.g., among other UE devices serviced by the cellular service provider).

The base station 102 may include at least one antenna 434, and possibly multiple antennas. The (at least one) antenna 434 may be configured to operate as a wireless transceiver and may be further configured to communicate with UE devices 106 via radio circuitry 430. The antenna 434 communicates with the radio circuitry 430 via communication chain 432. Communication chain 432 may be a receive chain, a transmit chain or both. The radio circuitry 430 may be designed to communicate via various wireless telecommunication standards, including, but not limited to, LTE, LTE-A WCDMA, CDMA2000, etc. The processor 404 of the base station 102 may be configured to implement part or all of the methods described herein, e.g., by executing program instructions stored on a memory medium (e.g., a non-transitory computer-readable memory medium), for base station 102 to communicate with a UE device capable of detecting an imbalance between LAA and LTE communications performed by the UE device, and making adjustments to account for such imbalances. Alternatively, the processor 404 may be configured as a programmable hardware element, such as an FPGA (Field Programmable Gate Array), or as an ASIC (Application Specific Integrated Circuit), or a combination thereof. In the case of certain RATs, for example Wi-Fi, base station 102 may be designed as an access point (AP), in which case network port 470 may be implemented to provide access to a wide area network and/or local area network (s), e.g. it may include at least one Ethernet port, and radio circuitry 430 may be designed to communicate according to the Wi-Fi standard. Base station 102 may operate according to the various methods as disclosed herein for communicating with mobile devices capable of detecting an imbalance between LAA and LTE cellular wireless communications of the mobile devices, and adjusting their wireless operations accordingly, when applicable.

Figure 5:
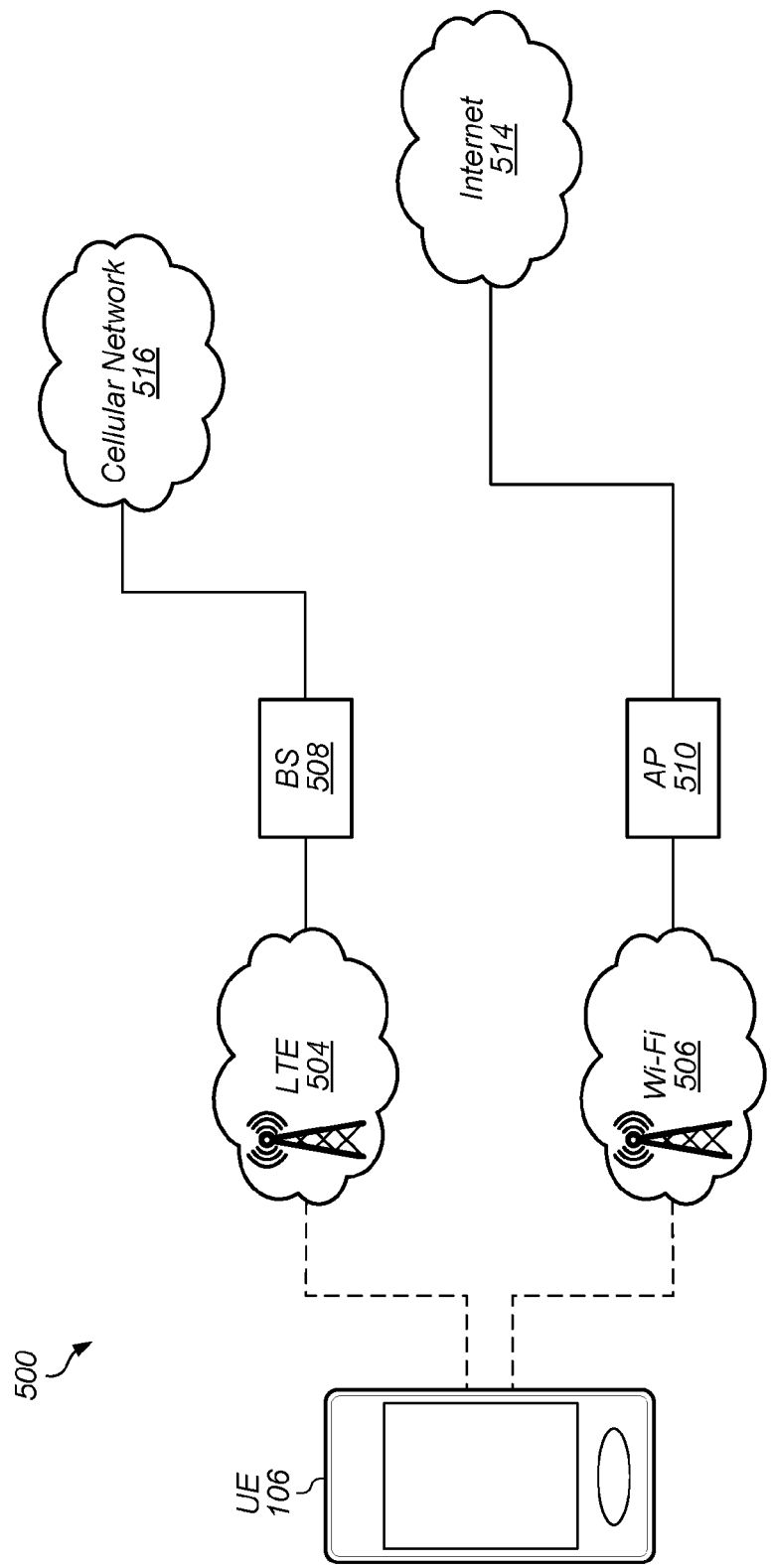
FIG. 5 illustrates an exemplary wireless communication system, according to some embodiments.

FIG. 5—Exemplary Communication System

FIG. 5 illustrates an exemplary wireless communication system 500 in accordance with some embodiments. System 500 is a system in which an LTE access network and a Wi-Fi radio access network are implemented. The system 500 may include UE 106 and LTE network 504 and Wi-Fi network 506.

LTE access network 504 is an exemplary representative of some embodiments of a first RAT access and Wi-Fi access network 506 is an exemplary representative of some embodiments of a second RAT access. LTE access network 504 may be interfaced with a broader cellular network (e.g. LTE network) and Wi-Fi access network 506 may be interfaced with the Internet 514. More particularly, LTE access network 504 may be interfaced with a serving base station (BS) 508, which may in turn provide access to broader cellular network 516. The Wi-Fi access network 506 may be interfaced with an access point (AP), which may in turn provide access to the Internet 514. UE 106 may accordingly access Internet 514 via AP 510 and cellular network 516 via LTE access network 504. In some embodiments, though not shown, UE 106 may also access Internet 514 via LTE access network 504. More specifically, LTE access network 504 may be interfaced with a serving gateway, which may in turn be interfaced with a packet data network (PDN) gateway. The PDN gateway may, in turn, be interfaced with Internet 514. UE 106 may accordingly access Internet 514 via either or both of LTE access network 504 and Wi-Fi access network 506.

Figure 6:
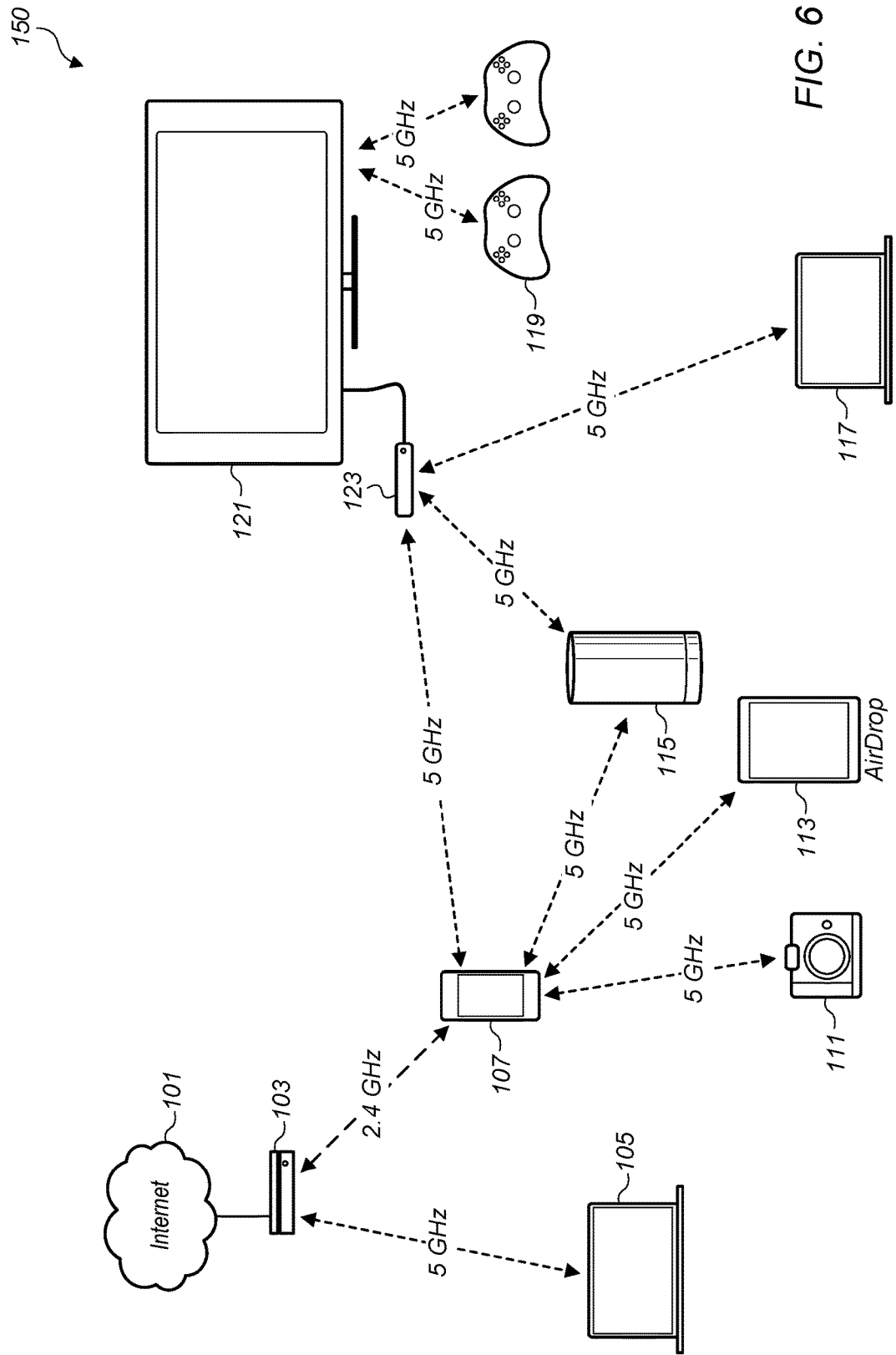
FIG. 6 shows an exemplary communication system in which multiple different devices may communicate with each other over specific band, such as 2.4 GHz and/or 5 GHz frequency bands using Wi-Fi.

FIG. 6—Exemplary Communication System with Multiple Wi-Fi Devices

FIG. 6 shows an exemplary communication system in which multiple different devices may communicate with each other over specific frequency bands, such as 2.4 GHz and/or 5 GHz frequency bands using Wi-Fi RAT. 5 GHz Wi-Fi (IEEE 802.11 ac/n) capable devices have become quite common, operating in both peer-to-peer mode and/or station mode, as shown in FIG. 6. Data communications over specific frequency bands, e.g. over the 5 GHz band may include voice, video, real time and best effort type of traffic. Illustrated devices include cameras (111), tablets (113), media servers/mini-servers (115), portable computers (105, 117), access ports/routers (103), game controllers (119), mobile devices such as smart phones (107), and smart monitors (121) or monitors with wireless access interface (121 together with 123). As shown in FIG. 6, many of the devices may communicate over the 5 GHz band, using Wi-Fi communication technology. In some cases the Wi-Fi communications conducted by the devices may be affected by LAA/LTE-U communications also taking place over the 5 GHz band. In general, the devices exemplified in FIG. 6 may communicate over a first frequency band according to one or more different RATs, and may further communicate over a second frequency band according to at least one of the RATs used to communicate over the first frequency band. Accordingly, issues may arise when a device communicates over both (the first and second) frequency bands according to a first RAT while communication over at least one of two frequency bands is also taking place according to a second RAT. Various embodiments disclosed herein aim to reduce and/or eliminate degradation of data throughput and/or decreased performance of streaming applications caused by the coexistence, in the same frequency band, of signals respectively transmitted according to two different RATs.

Presence of LAA/LTE-U Signals

In LTE, carrier aggregation (CA) refers to the aggregation of two or more component carriers (CCs) in order to support wider transmission bandwidths, e.g. bandwidths of up to 100 MHz. A UE may simultaneously receive or transmit on one or multiple CCs depending on the UE's capabilities. When CA is configured, the UE may maintain one RRC connection with the network. The serving cell managing the UE's RRC connection is referred to as the Primary Cell (PCell), and Secondary Cells (SCells) together with the PCell may form a set of serving cells. In CA, a UE may be scheduled via PDCCH over multiple serving cells simultaneously. Cross-carrier scheduling with the Carrier Indicator Field (CIF) allows the PDCCH of a serving cell to schedule resources on another serving cell. That is, a UE receiving a downlink assignment on one CC may receive associated data on another CC.

Figure 7:
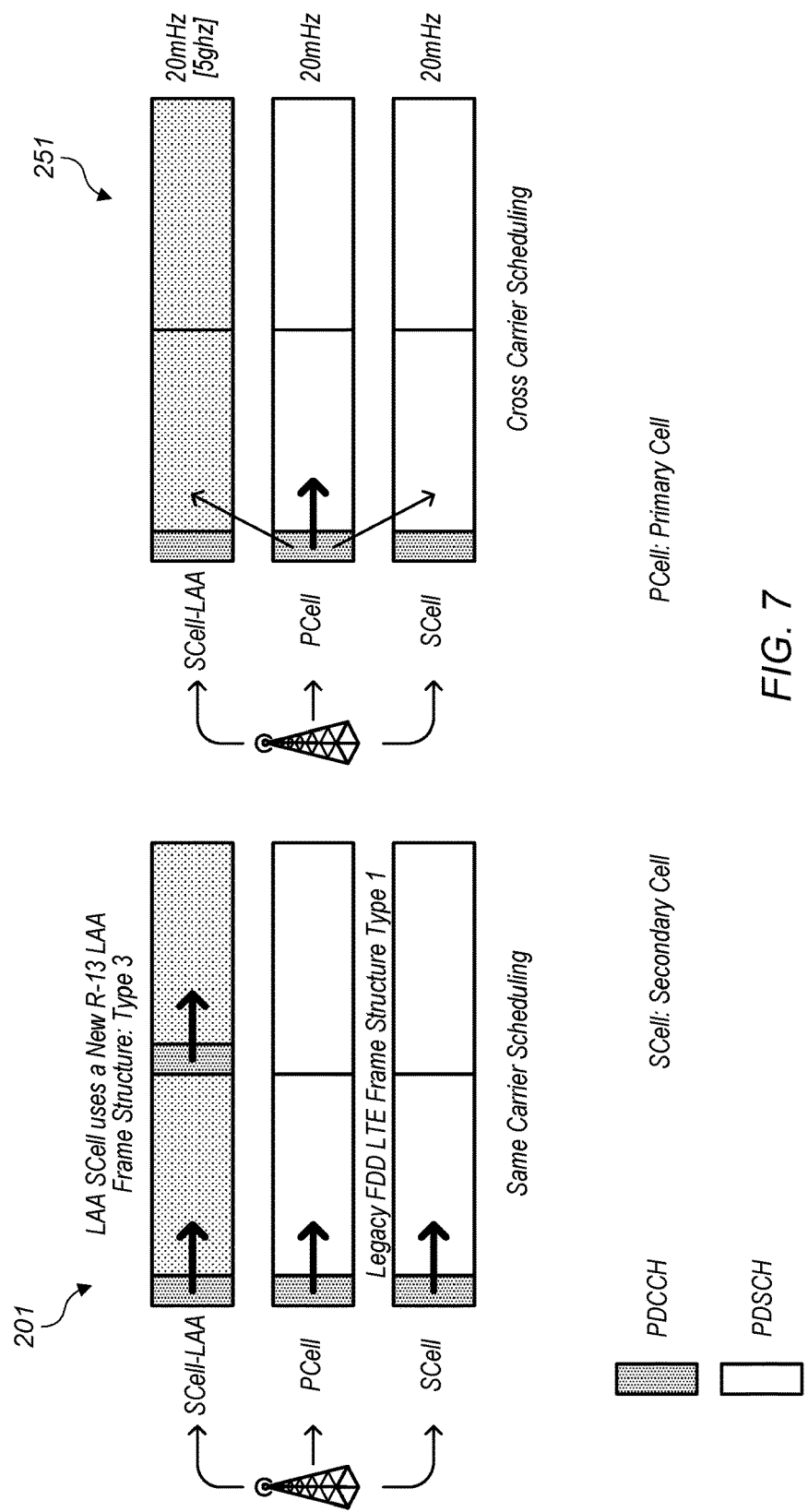
FIG. 7 shows an example of typical LAA control and data scheduling.

LAA is a sub-category of LTE inter-band carrier aggregation, where one of the secondary carriers is operating in a 5 GHz unlicensed band, a band over which communications according to another RAT, such as Wi-Fi, may also be taking place. Resources in an LAA carrier are scheduled in the same manner that resources are scheduled in legacy carrier aggregation (CA). That is, carrier scheduling and/or cross layer scheduling for LAA carriers are the same as for other CA carriers (PDCCH or ePDCCH). An LAA SCell may operate in a frame structure type 3 (shown in FIG. 7) composed of 20 slots and may be accessed following a successful listen-before-talk (LBT) procedure. FIG. 7 shows an example of typical LAA control and data scheduling, providing a respective example for same carrier scheduling (201) and a respective example for cross carrier scheduling (251), assuming a successfully completed LBT procedure in the previous subframe. If a start position of the RRC subframe indicates 's07', and no DCI is received in slot 1, the UE may read the PDCCH/ePDCCH of slot 2 to check downlink data availability.

Use of Unlicensed Spectrum and LAA

Cellular traffic is expected to grow exponentially in the future. For example, mobile data traffic is forecast to increase from 3.7 Exabytes, or EB (~$3.7*10^{18}$ bytes) per month in 2015 to 30.6 EB per month in 2020. However, the Licensed Spectrum is considered a major bottleneck preventing operators from expanding network capacity. During the latest Advanced Wireless Services (AWS)-3/79 spectrum auction, U.S operators spent upwards of $44.9 Billion in the 65 MHz spectrum. The 5 GHz unlicensed band on the other hand represents up to 500 MHz of available bandwidth at zero auction cost. Therefore, LAA represents at least one approach applicable to solving this very same spectrum problem.

Imbalanced Resource Allocation in Devices Supporting LAA

As previously mentioned, LAA is a solution for cellular operators to expand their operations beyond licensed radio spectrum. The availability of a licensed and regulated spectrum typically results in more robust wireless communications, with guaranteed QoS, over LTE and cellular networks when contrasted with wireless communications over Wi-Fi. The unlicensed spectrum is, by default, a "best effort" spectrum where multiple equipment from multiple vendors and technologies can coexist. The QoS for wireless communications conducted in the unlicensed spectrum depends greatly on the number of devices concurrently in use and the level of signal interference. By mixing licensed spectrum and unlicensed spectrum usage for cellular devices (UEs) and hiding the nature of the connection to the user of those devices, operators can conceivably relegate some wireless cellular devices to extensively operate in the unlicensed spectrum. For example, cellular service operators may too frequently offload cellular communications of a UE to the unlicensed spectrum, e.g. as LAA 3GPP communications, even when bandwidth in the licensed spectrum is available.

In a worst case scenario, a cellular operator may offload all of the communications/traffic of UEs associated with (or belonging to) a specific group or type of subscribers to the unlicensed spectrum, in order to keep their licensed spectrum at a low load for wireless communication devices associated with preferred customers. This can artificially degrade the performance of many home/enterprise/Wi-Fi devices operating in the same band (e.g. in the 5 GHz band), resulting in a poor user experience for users/owners of those devices. In this case, UEs that do not support LAA may actually be at an advantage, allowing those devices to operate only in the better spectrum (e.g. the licensed spectrum). In such imbalanced allocations, the eNB server may transmit user data only or mostly over an LAA SCell, while the PCell (in the licensed spectrum) is used only for signaling. This may lead to higher power consumption in the affected UEs, and may also result in a lower QoS compared to non LAA devices operating only in the licensed spectrum/band(s).

Detection of Imbalance for Communications Conducted in Licensed and Unlicensed Bands In one set of embodiments, a safeguard mechanism may be provided in order to detect when a cellular service operator/network excessively offloads some wireless communication devices to operate in the unlicensed spectrum, and possibly deactivate (in flight, or dynamically) the LAA (CA) feature in those affected wireless communication devices to effectively force the operator to provide use of the licensed spectrum to those affected devices. For example, by detecting an imbalance whereby a wireless communication device is excessively relegated to operate in a second frequency spectrum as opposed to operating in a first frequency spectrum, where the second frequency spectrum may be an unlicensed frequency spectrum and the first frequency spectrum may be a licensed frequency spectrum, the wireless communication device may make certain adjustments that result in the wireless communication device no longer excessively operating in the second frequency spectrum, and causing the wireless communication device to operate in the first frequency spectrum instead. The imbalance in radio resource allocation patterns and thresholds may be defined according to at least device, type of applications, type of radio bearers, and/or IP flows. For example, when a percentage or portion of all wireless communications of a wireless communication device is in the second spectrum, when that percentage or portion represents an imbalance may be defined or determined/specified based at least on device, type of applications, type of radio bearers, and/or IP flows.

Accordingly, in some embodiments, a wireless communication device (e.g. UE 106) may conduct wireless communications over (or in) a first specified frequency band (or spectrum) according to a first radio access technology (RAT), where the first RAT is a cellular wireless communication standard, e.g. 3GPP/LTE. The wireless communication device may also simultaneously (with respect to conducting the wireless communications over the first specified frequency band) conduct wireless communications over (or) in a second specified frequency band (or spectrum) according to the first RAT. The first frequency band may be a licensed band associated with the first RAT, e.g. a licensed band associated with 3GPP/LTE communications, and the second frequency band may be an unlicensed band associated with the first RAT, which may be a frequency band that is also associated with a second RAT, e.g. a 5 GHz band also associated with Wi-Fi communications. The wireless communication device may detect an imbalance between the communications conducted according to the first RAT over the first frequency band (or spectrum) and the second frequency band (or spectrum), and upon detecting this imbalance the wireless communication device may take corrective action(s) that causes or results in the wireless communication device operating in the first frequency band or perform a greatly reduced portion of its total wireless communications over the second frequency band with respect to the communications performed over the first specified frequency band. Specifically, the wireless communication device may detect when more of the wireless communications are conducted over the second specified frequency band (e.g. over the unlicensed band) than what may be intended, and make adjustments to have the wireless communication device conduct more of the wireless communications according to the first RAT over the first specified frequency band (e.g. over the licensed band) rather than over the second specified frequency band.

Frequency Spectrum Radio Resource Allocation and Monitoring

In some embodiments, a wireless communication device (UE) may monitor unlicensed/licensed radio resource allocation, and may detect when there is an imbalance in resource allocation. For example, the UE may detect when more of the wireless communications of the UE are conducted over an unlicensed band than desired, for example when more (or a higher portion) of the wireless communications are simultaneously conducted in an unlicensed band than in a licensed band. In some cases all or a majority of the cellular communications of the UE may be conducted over/in the unlicensed band instead of those wireless communications being conducted over/in the licensed band. In some embodiments, the UE may perform the monitoring and detecting by executing a radio link monitoring algorithm integrated into the MAC layer (associated with the carrier aggregation). The UE may track the SCell ID and the nature of the spectrum (licensed or unlicensed) in the MAC layer. For example, the UE may consider as inputs (into the algorithm) the grants received each transmit time interval (TTI) from the base station currently serving the UE. Each grant may be associated with either a SCell or a PCell. Each grant associated with the SCell may be considered an instance of or occurrence of imbalance. For example, when the UE receives a grant from the network (e.g. from the base station or eNB currently serving the UE in the network) and the grant is associated with a SCell, the UE may interpret the grant as one instance/occurrence of imbalance.

In some embodiments, a dynamic or statistical threshold may be defined between allocation of licensed and unlicensed radio resources in the MAC layer. A different threshold may be defined for different types of network traffic associated with different QoS (e.g. VoLTE, Best Effort, etc.) For example, for VoLTE traffic, a threshold representative of a very low tolerance may be specified with respect to receiving VoLTE grants associated with unlicensed SCells. In another example, for best effort traffic, a threshold representative of a higher tolerance may be specified with respect to receiving grants associated with an unlicensed spectrum without receiving (at least) an equivalent number of grants associated with a licensed spectrum. If an imbalance is detected, the UE may make appropriate adjustments. In some cases, in response to detecting an imbalance, the LAA SCell may be deactivated, while in other cases the carrier aggregation itself may be deactivated.

The wireless communication device may adjust for the radio resource allocation imbalance in several ways. In some embodiments, the imbalance may be alleviated by using the IDC indication from the UE to eNB, the Release 11 IDC indication, release 13 IDC indication for LAA/Wi-Fi sharing, or the Channel Quality Indicator (CQI) reporting for the SCell, to deactivate the SCell. Accordingly, CQI—as well as downlink HARQ ACK/NACK indicators and other information—may be reported to the base station via the Uplink Control Information UCI) Information Element (IE). Since there is one Physical Uplink Control Channel (PUCCH) associated with (or corresponding to) a PCell regardless of the number of carrier channels (CCs), the UCI for each CC may be reported via the same PUCCH. In order to deactivate unlicensed data reception, the UE may simply request a network (e.g. the base station serving the UE in the given network) to deactivate the SCell(s) operating in the unlicensed spectrum, by the UE transmitting a CQI value of zero (0) via PUCCH reporting to the base station. Upon receiving a CQI value of 0 associated with (or corresponding) to a respective SCell, the base station may interpret the CQI value of zero as an indication that the SCell is out of range and that the SCell is to be deactivated. The activation and deactivation of the SCell may be completely transparent to the upper layer(s) and therefore doesn't impact ongoing transmissions/communications (e.g. data and/or VoIP sessions) in any way. The network (e.g. the base station serving the UE within the network) may then deactivate the SCell, and schedule data transmission for the UE through available PCell/SCell(s) operating in the licensed spectrum for the next TTI.

In some embodiments, more generally, the UE may send a report or reports to the base station which include values for various indicators and/or metrics that may cause the base station to disable the SCell(s) associated with the unlicensed band(s). For example, the UE may report Reference Signal Received Power (RSRP) and/or Reference Signal Received Quality (RSRQ) values for the SCell(s) to the network (e.g. to the base station serving the UE) that indicate to the network that the SCell(s) ought to be deactivated for communications of the UE. Another example may include the UE reporting that the UE has a low Power Headroom (PHR) for the SCell(s), where PHR may indicate how much transmission power is left for the UE to use in addition to the power being used by a current transmission. The PHR is a type of Media Access Control (MAC) Control Element (CE) that reports the PHR between the current transmission power (estimated power) and the nominal power. The base station may receive the PHR value to estimate how much uplink bandwidth the UE may use for a specific subframe. When receiving a low PHR, the network may interpret the low PHR as an incapability of the UE for further concurrent transmission using the SCell(s), and may therefore deactivate the SCell(s) for use in wireless transmissions of the UE.

Figure 8:
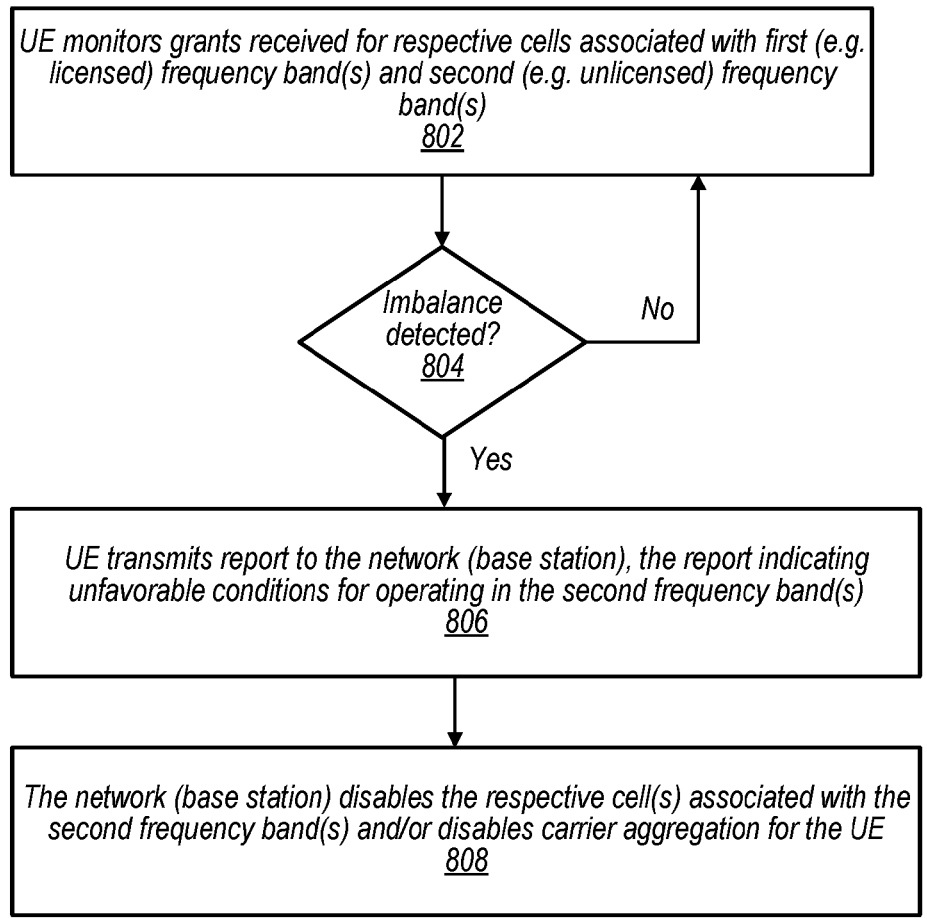
FIG. 8 shows an exemplary flowchart for mitigating an imbalance between wireless communications conducted over licensed and unlicensed bands, respectively, according to some embodiments.

FIG. 8—Flow Diagram of Exemplary Method for Radio Resource Allocation Imbalance Detection and Mitigation FIG. 8 shows a flow diagram of an exemplary method for detecting and mitigating radio resource allocation imbalance, for example when a higher than desired percentage of a wireless communication device's communications simultaneously conducted over a licensed spectrum (or frequency band) and unlicensed spectrum (or frequency band) are scheduled in the unlicensed spectrum (or frequency band). A UE (for example UE 106) may monitor grants received for respective cells associated with one or more first (e.g. licensed) frequency band(s) and one or more second (e.g. unlicensed) frequency band(s) in which the UE is simultaneously communicating (802). In some embodiments, the UE may track all such grants received for a transmit time interval (TTI), and may base imbalance detection decisions on a per TTI basis. In some embodiments the UE may track grants received within any specified time duration. In general, the imbalance may be determined with respect to how much, or what portion of all wireless communications conducted by the UE according to a specific RAT are in the second frequency band. In some embodiments this may be considered with respect to how much, or what portion of all wireless communications conducted by the UE are in the first frequency band. Since the UE is simultaneously communicating according to the specific RAT in the first frequency band and the second frequency band, a first portion of the UE's overall (total) wireless communications is over the first frequency band and a remaining (second) portion of the UE's overall communications is over the second frequency band.

If the UE detects an imbalance ("Yes" branch at 804), it may transmit a report to the network (e.g. to the base station serving the UE), with the report indicating unfavorable conditions for the UE to be operating in the second frequency band(s) (806). In response to receiving such a report, the network may disable the respective cell(s) associated with the second frequency band(s) and/or it may disable carrier aggregation for the UE (808).

Embodiments of the present invention may be realized in any of various forms. For example, in some embodiments, the present invention may be realized as a computer-implemented method, a computer-readable memory medium, or a computer system. In other embodiments, the present invention may be realized using one or more custom-designed hardware devices such as ASICs. In other embodiments, the present invention may be realized using one or more programmable hardware elements such as FPGAs.

In some embodiments, a non-transitory computer-readable memory medium (e.g., a non-transitory memory element) may be configured so that it stores program instructions and/or data, where the program instructions, if executed by a computer system, cause the computer system to perform a method, e.g., any of a method embodiments described herein, or, any combination of the method embodiments described herein, or, any subset of any of the method embodiments described herein, or, any combination of such subsets.

In some embodiments, a device (e.g., a UE) may be configured to include a processor (or a set of processors) and a memory medium (or memory element), where the memory medium stores program instructions, where the processor is configured to read and execute the program instructions from the memory medium, where the program instructions are executable to implement any of the various method embodiments described herein (or, any combination of the method embodiments described herein, or, any subset of any of the method embodiments described herein, or, any combination of such subsets). The device may be realized in any of various forms.

Although the embodiments above have been described in considerable detail, numerous variations and modifications will become apparent to those skilled in the art once the above disclosure is fully appreciated. It is intended that the following claims be interpreted to embrace all such variations and modifications.

The invention claimed is:

1. An apparatus comprising:
 a processing element configured to cause a wireless communication device to:
  conduct wireless communications according to a first radio access technology (RAT) simultaneously in a first frequency band and in a second frequency band;
  detect a radio resource allocation imbalance based at least on the wireless communication device conducting a higher portion than a previously specified portion of the wireless communications in the second frequency band with respect to the first frequency band; and
  in response to detecting the radio resource allocation imbalance, cause a base station serving the wireless communication device to schedule subsequent wireless communications of the wireless communication device in the first frequency band.

2. The apparatus of claim 1, wherein the first frequency band is a licensed frequency band for the wireless communications and the second frequency band is an unlicensed frequency band for the wireless communications.

3. The apparatus of claim 1, wherein the processing element is further configured to cause the wireless communication device to detect the radio resource allocation imbalance by executing an algorithm integrated into a media access control layer.

4. The apparatus of claim 1, wherein the processing element is further configured to cause the wireless communication device to detect the radio resource allocation imbalance by tracking grants respectively received from a primary cell associated with the first frequency band and a secondary cell associated with the second frequency band.

5. The apparatus of claim 1, wherein the processing element is further configured to cause the wireless communication device to detect the radio resource allocation imbalance by detecting that the wireless communication device successively received at least a specified number of grants from a secondary cell associated with the second frequency band.

6. The apparatus of claim 1, wherein the processing element is further configured to cause the wireless communication device to detect the radio resource allocation imbalance by detecting that the wireless communication device has received a first number of grants from a primary cell associated with the first frequency band and a second number of grants from a secondary cell associated with the second frequency band, and the second number exceeds the first number by at least a specified amount.

7. The apparatus of claim 6, wherein the specified amount is different for each different type of traffic included in the wireless communications.

8. The apparatus of claim 1, wherein the processing element is further configured to cause the wireless communication device to detect the radio resource allocation imbalance by counting how many grants are received by the wireless communication device during a transmit time interval from a primary cell associated with the first frequency band and how many grants are received by the wireless communication device during the transmit time interval from a secondary cell associated with the second frequency band.

9. The apparatus of claim 1, wherein the base station scheduling the subsequent wireless communications of the wireless communication device in the first frequency band is through one of:
   deactivation of a secondary cell associated with the second frequency band; or
   deactivation of carrier aggregation for the wireless communication device.

10. The apparatus of claim 9, wherein the processing element is further configured to cause the wireless communication device to transmit a channel quality indicator value of zero for the secondary cell to the base station to cause the deactivation of the secondary cell by the base station.

11. The apparatus of claim 1, wherein the processing element is further configured to cause the wireless communication device to transmit a report to the base station to cause the base station to schedule the subsequent wireless communications of the wireless communication device in the first frequency band, wherein the report is indicative of unfavorable conditions for the wireless communication device to operate in the second frequency band.

12. A wireless communication device comprising:
   radio circuitry configured to facilitate wireless communications of the wireless communication device according to a first radio access technology (RAT) simultaneously in a first frequency band and in a second frequency band; and
   a processing element configured to interoperate with the radio circuitry to cause the wireless communication device to:
      detect a radio resource allocation imbalance based at least on the wireless communication device conducting a higher portion than a previously specified portion of the wireless communications in the second frequency band with respect to the first frequency band; and
      in response to detecting the radio resource allocation imbalance, cause a base station serving the wireless communication device to schedule subsequent wireless communications of the wireless communication device in the first frequency band.

13. The wireless communication device of claim 12, wherein the processing element is configured to interoperate with the radio circuitry to further cause the wireless communication device to detect the radio resource allocation imbalance through one or more of the following:
   execution of an algorithm integrated into a media access control layer;
   tracking of grants respectively received from a primary cell associated with the first frequency band and a secondary cell associated with the second frequency band;
   detection of the wireless communication device successively receiving at least a specified number of grants from the secondary cell;
   detection of the wireless communication device receiving a first number of grants from the primary cell and a second number of grants from the secondary cell, wherein the second number exceeds the first number by at least a specified amount; or
   a count of how many grants are received by the wireless communication device during a transmit time interval from the primary cell and how many grants are received by the wireless communication device during the transmit time interval from the secondary cell.

14. The wireless communication device of claim 13, wherein for the detection of the wireless communication device receiving a first number of grants from the primary cell and a second number of grants from the secondary cell, the specified amount is different for each different type of traffic included in the wireless communications.

15. The wireless communication device of claim 12, wherein the base station scheduling the subsequent wireless communications of the wireless communication device in the first frequency band is through one of:
   deactivation of a secondary cell associated with the second frequency band; or
   deactivation of carrier aggregation for the wireless communication device.

16. The wireless communication device of claim 15, wherein the processing element is configured to interoperate with the radio circuitry to further cause the wireless communication device to transmit a channel quality indicator value of zero for the secondary cell to the base station to cause the deactivation of the secondary cell by the base station.

17. A non-transitory memory element storing instructions executable by a processing element to cause a wireless communication device to:
   conduct wireless communications according to a first radio access technology (RAT) simultaneously in a first frequency band and in a second frequency band;
   detect a radio resource allocation imbalance based at least on the wireless communication device conducting a higher portion than a previously specified portion of the wireless communications in the second frequency band with respect to the first frequency band; and
   in response to detecting the radio resource allocation imbalance, cause a base station serving the wireless communication device to schedule subsequent wireless communications of the wireless communication device in the first frequency band.

18. The non-transitory memory element of claim 17, wherein the instructions are executable by the processing element to cause the wireless communication device to detect the radio resource allocation imbalance through one or more of the following:
   execution of an algorithm integrated into a media access control layer;
   tracking of grants respectively received from a primary cell associated with the first frequency band and a secondary cell associated with the second frequency band;
   detection of the wireless communication device successively receiving at least a specified number of grants from the secondary cell;
   detection of the wireless communication device receiving a first number of grants from the primary cell and a second number of grants from the secondary cell, wherein the second number exceeds the first number by at least a specified amount; or
   a count of how many grants are received by the wireless communication device during a transmit time interval from the primary cell and how many grants are received by the wireless communication device during the transmit time interval from the secondary cell.

19. The non-transitory memory element of claim 18, wherein for the detection of the wireless communication device receiving a first number of grants from the primary cell and a second number of grants from the secondary cell, the specified amount is different for each different type of traffic included in the wireless communications.

20. The non-transitory memory element of claim 17, wherein the base station scheduling the subsequent wireless communications of the wireless communication device in the first frequency band is through one of:
   deactivation of a secondary cell associated with the second frequency band; or
   deactivation of carrier aggregation for the wireless communication device.

21. The non-transitory memory element of claim 17, wherein the instructions are executable by the processing element to further cause the wireless communication device to transmit a report to the base station to cause the base station to schedule the subsequent wireless communications of the wireless communication device in the first frequency band, wherein the report is indicative of unfavorable conditions for the wireless communication device to operate in the second frequency band.

\* \* \* \* \*